Figure 1:
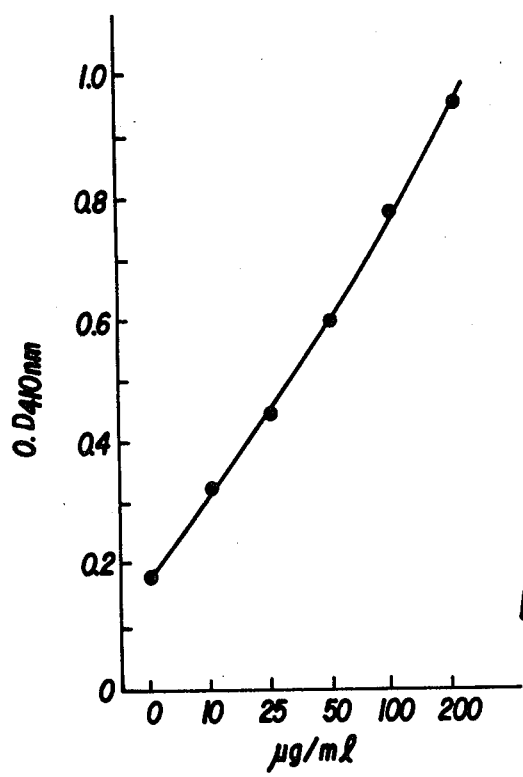

United States Patent [19]

Sunahara et al.

[11] 4,443,365

[45] Apr. 17, 1984

[54] METHOD FOR DETERMINATION OF THE VALPROIC ACID AND REAGENTS THEREIN

[75] Inventors: Noriyuki Sunahara, Kyoto; Shunsuke Naruto, Ikoma; Akira Kagemoto, Osaka; Shigeru Kurooka, Fujiidera; Kanae Yokogawa, Nara, all of Japan

[73] Assignee: Dainippon Pharmaceutical Company Limited, Osaka, Japan

[21] Appl. No.: 276,794

[22] Filed: Jun. 24, 1981

[30] Foreign Application Priority Data

Jul. 1, 1980 [JP] Japan .................................. 55-90403

[51] Int. Cl.³ .......................... C07G 7/00; C07G 7/02
[52] U.S. Cl. ............................ 260/112 R; 260/112 B; 260/121; 424/85; 435/7; 435/188
[58] Field of Search ............... 260/112 R, 112 B, 121; 424/85; 435/7, 188

[56] References Cited

U.S. PATENT DOCUMENTS

| | | | |
|---|---|---|---|
| 3,654,090 | 4/1972 | Schuurs et al. | 424/12 X |
| 3,839,153 | 10/1974 | Schuurs et al. | 424/12 X |
| 3,850,752 | 11/1974 | Schuurs et al. | 424/12 X |
| 3,879,262 | 4/1975 | Schuurs et al. | 424/12 X |
| 4,214,048 | 7/1980 | Kitagawa | 260/112 R X |
| 4,218,539 | 8/1980 | Weitman | 435/188 |
| 4,238,389 | 12/1980 | Leung et al. | 260/112 R X |
| 4,261,974 | 4/1981 | Buckler et al. | 260/112 R X |
| 4,329,281 | 5/1982 | Christenson et al. | 260/121 X |

OTHER PUBLICATIONS

Antiepileptic Drugs, (Raven Press, New York, 1978), pp. 147–151.
Clin. Chim. Acta, 81 1 (1977).
Pharmacol. Reviews, 29 103 (1977).

*Primary Examiner*—Howard E. Schain
*Attorney, Agent, or Firm*—Armstrong, Nikaido, Marmelstein & Kubovcik

[57] ABSTRACT

δ-substituted derivatives of valproic acid are provided for conjugation to antigenic compositions, particularly proteins and enzymes.

The antigenic conjugates are employed for the production of antibodies, which find particular use in immunoassays for the determination of valproate.

Also are disclosed a kit containing at least the conjugate and the antibody and determination method of valproate using the kit.

7 Claims, 2 Drawing Figures

METHOD FOR DETERMINATION OF THE VALPROIC ACID AND REAGENTS THEREIN

The present invention relates to the immunochemical determination of valproic acid.

Valproic acid is a lower fatty acid which was synthesized firstly by Burton in 1881 and has the following chemical formula:

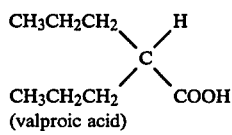
(valproic acid)

In 1963, Meunier discovered the antiepileptic activity of its sodium salt.

Nowadays, sodium valproate is widely used for the treatment of various types of epilepsy (minor seizure, focal seizure, psycomotor seizure and mixed seizure) or emotional behavior disturbance (ill temper, rage) accompanied by epilepsy.

It is well known that the valproate has side effects such as drowsiness, dizziness, headache, nausea, and emesis, anorexia, gastrointestinal disorder, constipation, general malaise, eruption, hepatic dysfunction etc., and the side effects tend to be manifested as the blood level of valproate increases. The blood level necessary for therapeutic effect is in the range of about 50–100 μg/ml.

It is also known that the blood level of valproate varies in the individual case even if the same dose per weight was administered to patient. This is due to differences among individuals in adsorption, distribution, metabolism, excretion and possible interaction of valproate with other drug administered in parallel. It has therefore been found necessary to keep suitable blood level by administering the drug based upon measured blood level of each patient in order to minimize the side effects.

For this reason, it has been desired to develop a rapid, precise and simple method for determination of valproic acid. Of the current assay procedures for valproic acid, a gas-liquid chromatography method is the most widely used. However, for the routine clinical use, this method has such disadvantages as requiring much amount of sample (0.5 to 1 ml or more of serum), pretreatment such as extraction and special apparatus.

The present inventors considered that, if antibody having specific affinity for valproic acid could be obtained, valproic acid might be determined by various immunochemical techniques (enzymoimmunoassay, radioimmunoassay, fluoroimmunoassay, spin immunoassay) which requires only small amount of sample and no pretreatment of the sample.

However, it has been considered that an antibody against valproic acid is difficult to produce because it has a simple lower fatty acid structure and various analogues of valproic acid are present in the blood of immunized animals.

The inventors synthesized several derivatives of valproic acid (Table 1) as haptens, prepared antigens by binding the haptens to protein and obtained antibodies by immunizing animals with the antigens. Then, the inventors prepared valproic acid derivatives labelled with an enzyme, checked their binding capacity with the antibodies through the reaction between antigens and antibodies, and investigated competitives binding capacity between valproic acid and labelled antigens against antibodies.

TABLE 1

| | | Properties of haptens | |
|---|---|---|---|
| No. | Haptens | Binding capacity between enzyme-labelled antigen and antibody* | Competitive binding capacity with valproic acid** |
| 1 | CH₃CH₂CH₂⧹ ⁄H <br> ⧸C⧹ <br> CH₃CH₂CH₂ COOH (Valproic acid) | ++ | − |
| 2 | CH₃CH₂CH₂⧹ ⁄H <br> ⧸C⧹ <br> CH₃CH₂CH₂ CONH(CH₂)₂COOH | ++ | − |
| 3 | CH₃CH₂CH₂⧹ ⁄H <br> ⧸C⧹ <br> CH₃CH₂CH₂ CONH—⟨◯⟩—NH₂ | ++ | − |
| 4 | CH₃CH₂CH₂⧹ ⁄H <br> ⧸C⧹ <br> CH₃CH₂CH₂ CONH(CH₂)₂COON(succinimide) | ++ | − |
| 5 | CH₃CH₂CH₂⧹ ⁄(CH₂)₂NH₂ <br> ⧸C⧹ <br> CH₃CH₂CH₂ COOH | ++ | + |

TABLE 1-continued

Properties of haptens

| No. | Haptens | Binding capacity between enzyme-labelled antigen and antibody* | Competitive binding capacity with valproic acid** |
|---|---|---|---|
| 6 | $H_2N(CH_2)_3$, $CH_3CH_2CH_2$, H, COOH | ++ | ++ |
| 7 | $H_2N(CH_2)_5$, $CH_3CH_2CH_2$, H, COOH | ++ | ++ |
| 8 | $HS(CH_2)_5$, $CH_3CH_2CH_2$, H, COOH | ++ | ++ |
| 9 | $OHC(CH_2)_3$, $CH_3CH_2CH_2$, H, COOH | ++ | ++ |
| 10 | $HOOC(CH_2)_4$, $CH_3CH_2CH_2$, H, COOH | ++ | ++ |

*In this column, ++ means that more than 80% of the labelled antigen was bound with the antibody when 200-fold dilution of antiserum was added to antigen-antibody system.
**Inhibition of antigen-antibody binding in the presence of sodium valproate (2 μg/tube).
++: more than 50%,
+: 10–50%,
—: less than 10%

The result is shown in Table 1. It can be clearly seen from Table 1 that binding capacity with the antigen was satisfactory in all the antibodies against the corresponding compounds, but highly competitive reaction between the labelled antigen and valproic acid was observed only in antibodies against the compounds No. 6–No. 10. The above result made it clear that the competitive reactivity between the labelled antigen and valproic acid was insufficient in antibodies against the compounds (No. 2–No. 5) in which (1) carboxyl group or (2) α-hydrogen atom of valproic acid was modified, and valproic acid itself (No. 1), whereas said competitive reactivity was sufficient in antibodies against the compounds (No. 6–No. 10) in which (3) at least one of the propyl group of valproic acid was modified. From other experiments, it was confirmed that said competitive reaction is little affected by metabolites of valproic acid, other drug or amino acid existing in blood. The inventors have completed the present invention after various research based upon the above findings. Accordingly, one object of the present invention is to provide compounds of the formula:

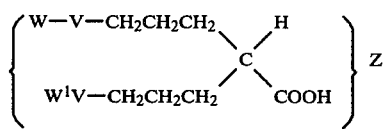

wherein
V is a bond or lower alkylene,
W is a bond to Z, or a linking group with two or three valency bonds, containing at least one atom selected from the group consisting of carbon, nitrogen, oxygen and sulfur,
$W^1$ is hydrogen atom, a bond to Z, or a linking group with two or three valency bonds, containing at least one atom selected from the group consisting of carbon, nitrogen, oxygen and sulfur,
Z is a protein, and salts thereof.

Another object of the present invention is to provide conjugate of compounds of the formula:

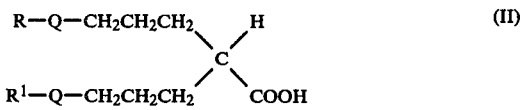

wherein
Q is a bond or lower alkylene,
R is —$NH_2$, —SH, —CHO, —COOH or —$COCH_2$-halogen,
$R^1$ is hydrogen atom, —$NH_2$, —SH, —CHO, —COOH or —$COCH_2$-halogen,
or salts thereof with an enzyme.

A further object of the present invention is to provide antibodies which are obtained by immunuzing an animal with a compound of the formula:

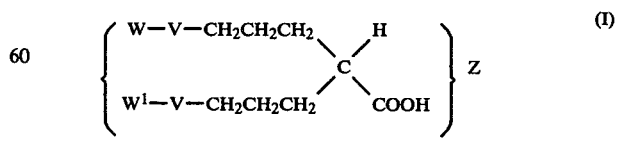

wherein
V is a bond or lower alkylene,
W is a bond to Z, or a linking group with two or three valency bonds, containing at least one atom selected from the group consisting of carbon, nitrogen, oxygen and sulfur, $W^1$ is hydrogen atom, a bond to Z, or a linking group with two or three valency bonds, containing at least one atom selected from the group consisting or carbon, nitrogen, oxygen and sulfur, and Z is a protein, or salts thereof.

Still further object of the present invention is to provide a kit suitable for immunoassay of valproic acid including separately stored component A and component B wherein Component A is an antibody which is obtained by immunizing an animal with a compound of the formula:

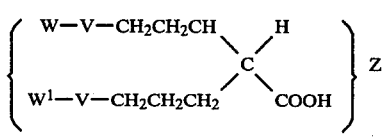

wherein

V is a bond or lower alkylene,

W is a bond to Z, or a linking group with two or three valency bonds, containing at least one atom selected from the group consisting of carbon, nitrogen, oxygen and sulfur, $W^1$ is hydrogen atom, a bond to Z, or a linking group with two or three valency bonds, containing at least one atom selected from the group consisting of carbon, nitrogen, oxygen and sulfur, Z is a protein, or salts thereof, and Component B is a compound of the formula:

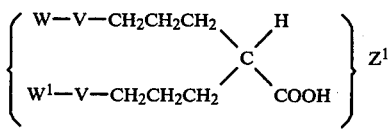

wherein

V is a bond or lower alkylene,

W is a bond to $Z^1$, or a linking group with two or three valency bonds, containing at least one atom selected from the group consisting of carbon, nitrogen, oxygen and sulfur, $W^1$ is hydrogen atom, a bond to $Z^1$, or a linking group with two or three valency bonds, containing at least one atom selected from the group consisting of carbon, nitrogen, oxygen and sulfur, $Z^1$ is an organic group having an enzymatic, fluorescent, radio or paramagnetic activity, or hydrogen atom, or salts thereof, provided that when $Z^1$ is hydrogen atom, V is a bond, W is a bond to $Z^1$, $W^1$ is hydrogen atom and any atom of the formula except carboxylic hydrogen has a radio activity.

Still further object of the present invention is to provide a method for determination of valproic acid which comprises (a) mixing a test sample containing valproic acid with an antibody which is obtained by immunizing an animal with a compound of the formula:

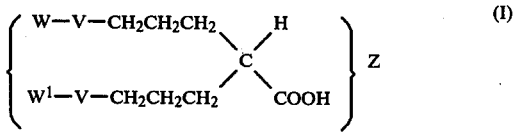

wherein

V is a bond or lower alkylene,

W is a bond to Z, or a linking group with two or three valency bonds, containing at least one atom selected from the group consisting of carbon, nitrogen, oxygen and sulfur, $W^1$ is hydrogen atom, a bond to Z, or a linking group with two or three valency bonds, containing at least one atom selected from the group consisting of carbon, nitrogen, oxygen and sulfur, Z is a protein, or salts thereof, and antigen or the formula:

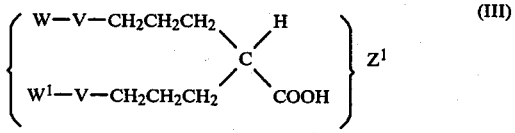

wherein

V is a bond or lower alkylene,

W is a bond to $Z^1$, or a linking group with two or three valency bonds, containing at least one atom selected from the group consisting of carbon, nitrogen, oxygen and sulfur, $W^1$ is hydrogen atom, a bond to $Z^1$, or a linking group with two or three valency bonds, containing at least one atom selected from the group consisting of carbon, nitrogen, oxygen and sulfur, $Z^1$ is an organic group having an enzymatic, fluorescent, radio or paramagnetic activity, or hydrogen atom, or salts thereof, provided that when $Z^1$ is hydrogen atom, V is a bond, W is a bond to $Z^1$, $W^1$ is hydrogen atom and any atom of the formula except carboxylic hydrogen has a radio activity (b) allowing the antibody to bind with valproic acid and the antigen competitively, and (c) measuring the activity of bound or free antigen.

In the above and subsequent description of the present specification, suitable examples and illustration of the various definitions to be included within the scope thereof are explained in details as follows.

The term "lower" in "lower alkylene" is intended to mean a group having 1 to 5 carbon atoms.

Suitable "lower alkylene" may include methylene, ethylene, propylene, trimethylene, tetramethylene and pentamethylene.

Suitable "linking group with two or three valency bonds, containing at least one atom selected from the group consisting of carbon, nitrogen, oxygen and sulfur" may include groups containing at least a group of the formula:

—X— or =Y— wherein X is —CO—, —NH— or —S— and Y is =CH— or =N—, and more particularly, groups of the formula:

—CO—[(U)$_p$(U$^1$)$_q$(U$^2$)$_r$],

—NH—[(U)$_p$(U$^1$)$_q$(U$^2$)$_r$],

—S—[(U)$_p$(U$^1$)$_q$(U$^2$)$_r$],

=CH—[(U)$_p$(U$^1$)$_q$],

=C$_f$=N—[(U)$_p$(U$^1$)$_q$(U$^2$)$_r$] and, —N=N— wherein
U is —NH—, —N=N—, —N=CH— or

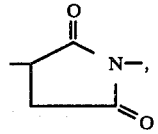

U$^1$ is lower alkylene, —O—lower alkylene- or lower arylene,
U$^2$ is —O—, —CO—, —COO— or —O—lower arylene,
p, q and r are each 0, 1 or 2, and t is 0 or 1 (wherein lower arylene may include phenylene, tolylene and xylylene),
and U, U$^1$, U$^2$ may be arranged in arbitrary order.

The preferable examples of said linking group and reagents used for obtaining such linking groups are shown in Table 2.

TABLE 2

| Linking group* (binding group in a protein) | reagent |
|---|---|
| —CO—(NH—) | CDI** |
| —NH—(CO—) | CDI |
| —CO—[NH—⟨phenyl⟩—O—](CO—) | H$_2$N—⟨phenyl⟩—OH, CDI |
| —NH—[(CH$_2$)$_4$—NH—](CO—) | phthalimide-N(CH$_2$)$_4$Br, CDI |
| [—N=CH—(CH$_2$)$_3$]—CH=(N—) | OHC(CH$_2$)$_3$CHO |
| —NH—[CO—(CH$_2$)$_2$—CO—](NH—) | succinic anhydride, CDI |
| —NH—[CH$_2$—CO—](NH—) | ClCH$_2$COOH, CDI |
| —N=N—(aromatic ring) | HNO$_2$ |
| —NH—[CO—⟨phenyl⟩—N=N—] (aromatic ring) | H$_2$N—⟨phenyl⟩—COOH, HNO$_2$, CDI |
| —NH—[CO—(CH$_2$)$_2$—CO—](O—⟨phenyl⟩—) | succinic anhydride, CDI |
| —NH—[CO—CH$_2$—](O—⟨phenyl⟩—) | ClCH$_2$COOH, CDI |
| =C=N[NH—⟨phenyl⟩—CO—](NH—) | H$_2$NHN—⟨phenyl⟩—COOH, CDI |
| =C=N—[O—CH$_2$—CO—](NH—) | H$_2$NOCH$_2$COOH, CDI |
| —CH=(N—) | CDI |

TABLE 2-continued

| Linking group* (binding group in a protein) | Linking group reagent |
|---|---|
| −NH−[CO−NH−C₆H₃(CH₃)−NH−CO] (NH−) | OCN−C₆H₃(CH₃)−NCO |
| −S−[−(CO)₂N−C₆H₄−N(CO)₂−] (S−) | [−(CO)₂N−C₆H₄−N(CO)₂−] |
| −NH−[CO−C₆H₄−N(CO)₂−] (S−) | [−(CO)₂N−O−CO−C₆H₄−N(CO)₂−] |
| −NH−[N=N−C₆H₄−C₆H₄−N=N−] (aromatic ring) | H₂N−C₆H₄−C₆H₄−NH₂, HNO₂ |
| −NH−[(CH₂)₅−](NH−) | OHC(CH₂)₃CHO, Na(CN)BH₃ |

*Group put in square brackets correspond to U,U¹ and U².
**CDI means carbodiimide reagents.

Suitable protein may include a albumin, globulin, thyroglobulin, shellish hemocyanin, edestin and enzymes. The protein may be fixed on water-insoluble substance.

Suitable salts may include conventional salts such as alkali metal salt, alkaline earth metal salt, ammonium salt and salt with organic amine, organic acid or inorganic acid.

The conjugate according to the invention can be prepared by reacting a compound (II) with functional group such as —NH₂, —SH, —COOH etc. of protein or modified protein, which is obtained by introducing functional group into the protein, directly or with a help of binding reagents, according to any means known to those skilled in the art.

Said means include glutaraldehyde method, periodate method, dimaleimide method, MBS method, mixed anhydride method, carbodiimide method, toluene diisocyanate method and diazo-method which were reported in Clin. Chim. Acta, 81, 1 (1977) and Pharmacol. Reviews, 29, 103(1977). The method of introducing mercapto group into protein was reported in Arch. Biochem. Biphys., 96, 605(1962) and that of introducing halogenoacetyl group was reported in Jour. Biol. Chem., 246, 2594(1971).

Suitable molar ratio of the compound (II): a protein may be 1–30:1 and the ratio can be controlled by changing the number of moles of the compound (II) used for reaction.

Some of the compounds (II) having —NH₂ or —COOH and their preparation method are described in Chem. Ber. 32, 3692 (1890), Jour. Am. Che. Soc., 71, 3312(1949), Monat.Chem., 69, 188 (1936), and others can be prepared, for example, according to the following processes.

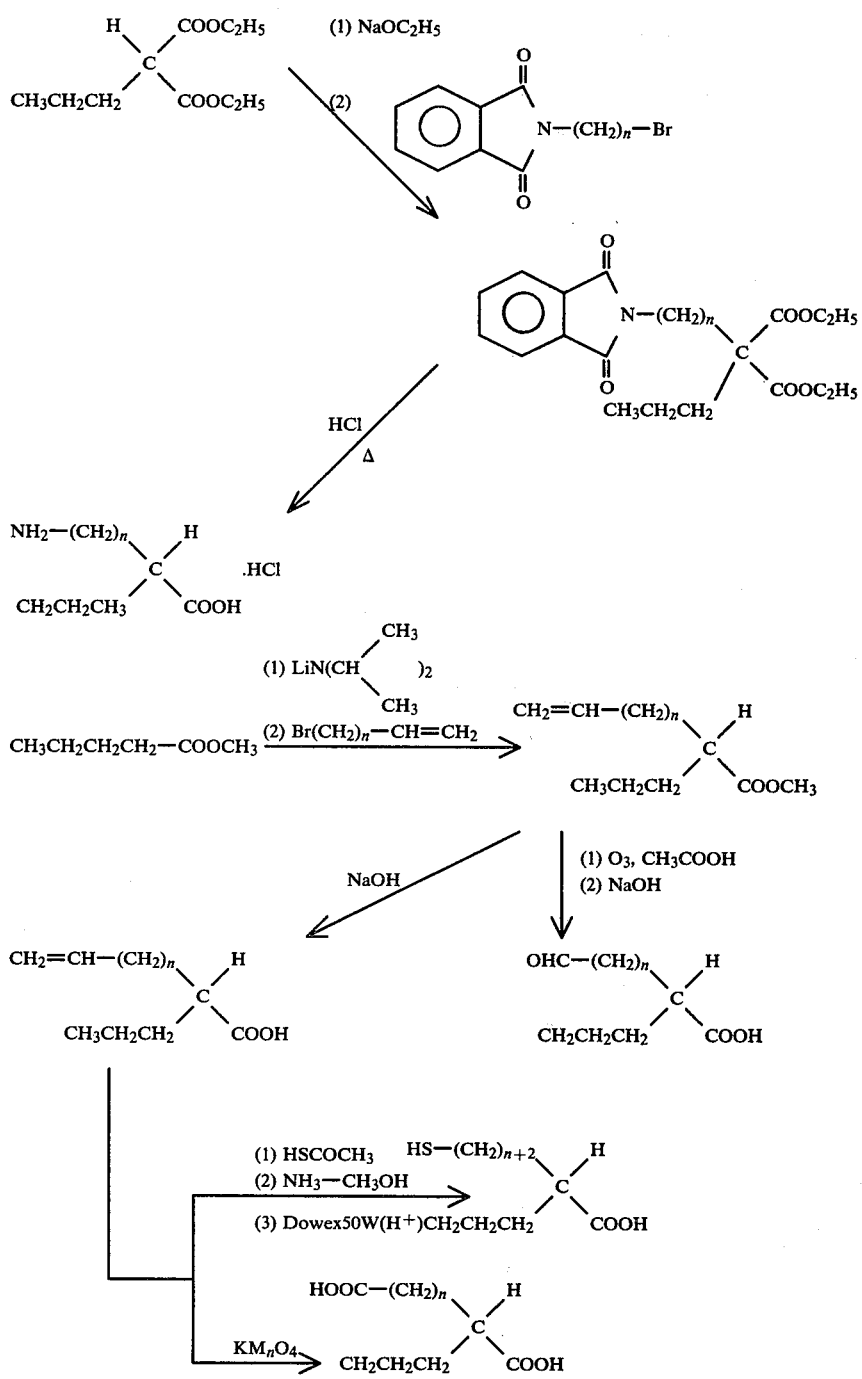

wherein $n \geq 3$

The antibodies for the immunochemical assay according to the invention can be prepared by injecting subcutaneously the conjugate with suitable adjuvant into an animal such as rabbit, guinea-pig, goat, sheep etc., bleeding and treating the obtained blood in the conventional manner.

Said antibodies may be insolubilized by binding with insoluble substances such as bacterial cell walls, natural insoluble polysaccharides such as cellulose, chemically treated dextran gels, agar gels, plastic beads, acrylamide gels, glass beads, metaloxide powders such as $Fe_3O_4$ etc., which facilitate the B/F separation process described after. The plastic beads include polypropylene beads, polyethylene beads, polycarbonate beads and polystyrene beads. The acrylamide gels include polymer gels prepared from acrylamide, N,N'-methylenebisacrylamide, N,N,N',N'-tetramethyl ethylenediamine and catalyst such as ammonium persulfate or riboflavin and light.

The insoluble substances can be bound to the antibodies by the conventional manner. For example, the plastic beads can be bound to the antibodies by dipping the plastic beads in a bicarbonate buffer (pH 9.6) solution containing an antibody. The bacterial cell walls can be bound chemically by using glutaraldehyde. The acrylamide gels can be bound chemically by diazo-coupling after reacting the acrylamide gels with ethylene diamine followed by p-nitrobenzoyl azide and sodium hydrosulfite. The glass beads can be bound chemically by using glutaraldehyde after silylating with 3-aminopropyl triethoxysilane. The cellulose can be bound chemically by activating with cyanogen bromide or converting into its azidocarbonylmethyl derivative. The agar gels and dextran gels can be bound by activating with cyanogen bromide. The $Fe_3O_4$ powders can be bound by granulating together with cellulose and activating with cyanogen bromide [Biotech. Bioeng., 15, 603 (1973)] or by granulating together with polyacrylamide agarose gel and using glutaraldehyde [Immunochemistry, 14, 443 (1977)]. The antibodies insolubilized by the last process are convenient because they can be separated with magnet.

In the component B of the kit according to the invention, suitable organic group having enzymatic activity may include a group derived from β-galuctosidase, peroxidase, lipase, alkaliphosphatase, glucose-6-phosphate dehydrogenase or glucose oxidase. These enzymes can be linked by the same technique as that described for a protein.

The suitable organic group having fluorescent activity may include a group derived from fluorescein, which can be introduced by using fluorescein isothiocyanate, for example, in the following manner.

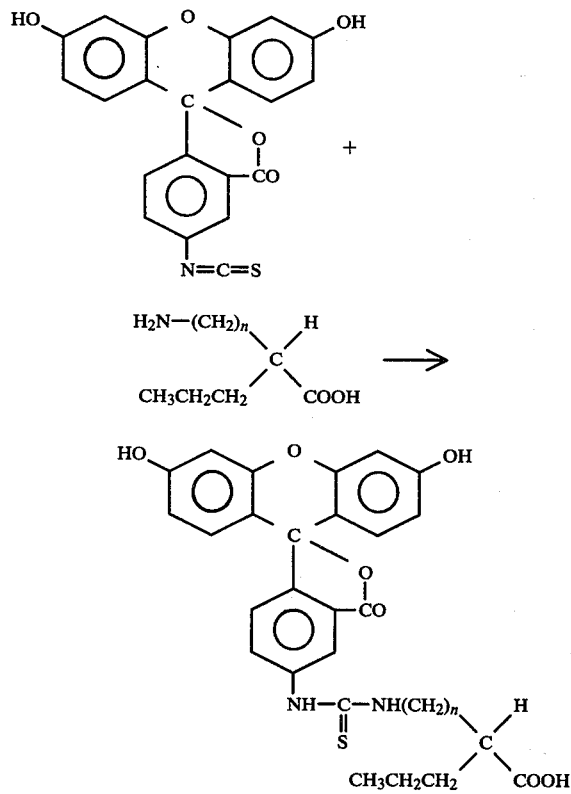

The suitable organic group having radio activity may include a group carrying $^{14}C$, $^{3}H$ or $^{125}I$, such as 3-iodo[$^{125}I$]-4-hydroxyphenyl, which can be introduced by using N-[3-(3-iodo[$^{125}I$]-4-hydroxyphenyl)-propyonyloxy] succinimide, for example, in the following manner.

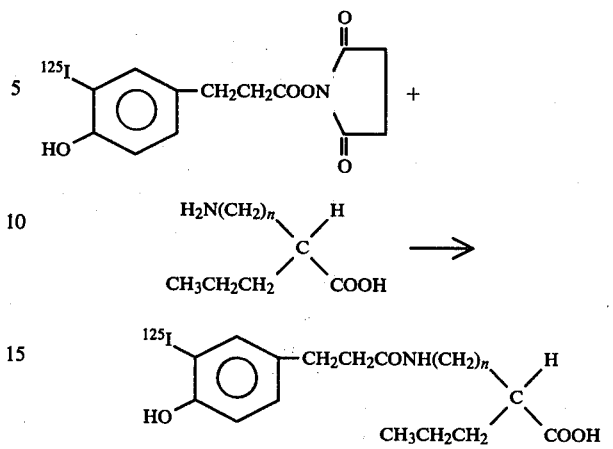

The suitable organic group having paramagnetic activity may include a group carrying unpaired electron, such as piperidinooxyl, which can be introduced by using 4-maleimido-2,2,6,6-tetramethylpiperidinooxyl in the following manner.

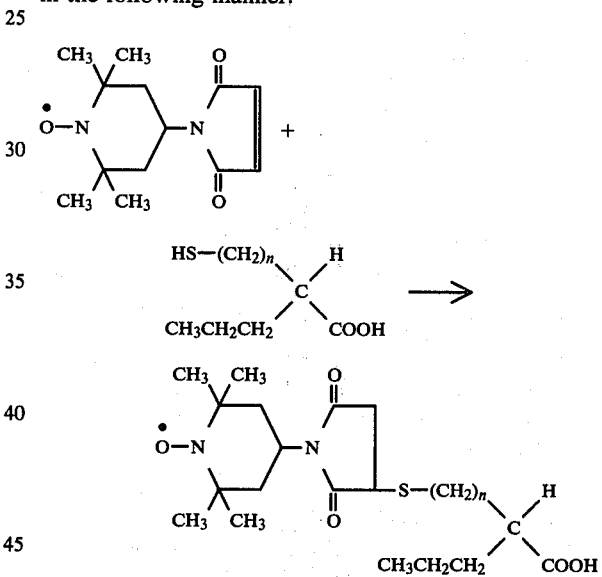

The component B of the kit according to the invention may also include valproic acid derivatives in which any atom of valproic acid except carboxylic hydrogen is substituted with a radioactive isotope.

In the kit according to the invention, it is not necessary that W, $W^1$ and V in the components A and B are identical. For example, a combination of a component A wherein W—V— is —NH— and $W^1$—V is H— with a component B wherein W—V is —S—$(CH_2)_2$— and $W^1$—V is H— can be used for the immunoassay according to the invention.

The kit may contain standard solutions of valproic acid for preparing the standard curve, reagents for measuring activity of the labelled antigen (for example, substrate, solvent for substrate and enzyme reaction stopping agent), the second antibody or buffering agent, in addition to the components A and B.

In the method for determination of valproic acid according to the invention, the bound and free antigens are separated before measuring the activity (B/F separation), when the antibody is insoluble. The B/F separation can be made, for example, by (1) fixing the antibody (component A) on insoluble substance such as bacterial cell walls before the reaction of antigen (component B), or (2) binding the antibody (component A) to second antibody against γ-globulin (IgG) before, after or during the reaction with antigen (component B). The second antibody is used as a solution in general, but can be fixed previously on insoluble substance. The insolubilization of second antibody has such advantages as to require smaller amount of the second antibody and shorter immuno-reaction time.

The activity of the labelled antigen can be measured by conventional method depending on the kind of labelling means.

The following examples further illustrate the invention, but should not be construed as a limitation thereto.

EXAMPLE 1

Preparation of 7-amino-2-propylheptanoic acid hydrochloride

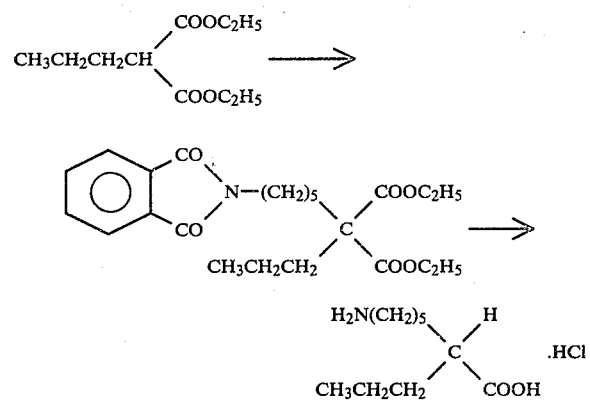

Sodium (0.5 g) was dissolved in ethanol (7 ml) and diethyl propylmalonate (4.4 g) was added to the solution. The resulting mixture was heated under reflux for 15 minutes. To the mixture was added N-(5-bromopentyl)phthalimide (6.4 g) and the mixture was further heated under reflux for 4 hours. Then, ethanol was removed by distillation. The residue was treated with ether and filtered. The filtrate was concentrated and the residue was chromatographed on silica gel column. A fraction eluted with 5% methanol in chloroform was recrystallized from a mixture of ether and hexane to give colorless crystals of diethyl 2-(5-phthalimidopentyl)-2-propylmalonate (m.p. 51°-52° C., yield 3.7 g).

A mixture of diethyl 2-(5-phthalimidopentyl)-2-propylmalonate (6 g) and 26% hydrochloric acid (36 ml) was heated in a sealed tube at 190° C. for 4 hours. After cooling, insoluble substance was removed by filtration. The filtrate was concentrated to dryness under reduced pressure and the residue was chromatographed on silica gel column. A fraction eluted with the upper phase of a mixture of butanol:acetic acid:water (4:1:5 volume by volume) was concentrated by dryness to give colorless sticky oil of the desired compound (yield 1.3 g).

Anal. calcd. for $C_{10}H_{21}NO_2 \cdot HCl \cdot \frac{1}{2}H_2O$: C,51.60;H,9.96;N,6.02;Cl,15.23%. Found: C,51.76;H,9.83;N,6.01;Cl,15.04%. M+1 ion in chemical ionization mass spectrometry: m/e 188.

EXAMPLE 2

Preparation of 7-mercapto-2-propylheptanoic acid

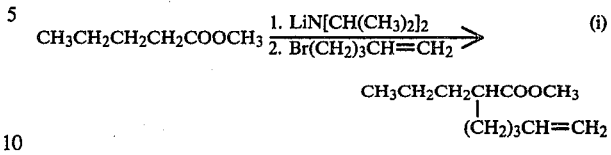

To a solution of lithium diisopropyl amide, which was prepared from diisopropylamine (6.6 g) in dry tetrahydrofuran (50 ml) and 15% butyl lithium in hexane solution (38 ml) at −65° to −60° C. in a nitrogen atmosphere, were added dropwise a solution of methyl pentanoate (7 g) in dry tetrahydrofuran (65 ml) followed by a solution of 5-bromo-1-pentene (9 g) in dry tetrahydrofuran (30 ml) at the same temperature. The mixture was stirred for 4 hours at −65° to 0° C. All the operations described above were carried out in a nitrogen atmosphere. Diluted hydrochloric acid (25 ml) and toluene (200 ml) were added at 0° C. to the mixture, which was further stirred. The organic layer was separated, washed with water, dried and concentrated. The resulting oily residue (9 g) was purified by silica gel column chromatography to give colorless oil of methyl 2-propyl-6-heptenoate (4.8 g).

Mass spectrometry: m/e 186 (M+ion)
IR spectrum: 1730, 1640 cm$^{-1}$ (neat)
Rf value (TLC on silica, 2% methanol-hexane) 0.7.

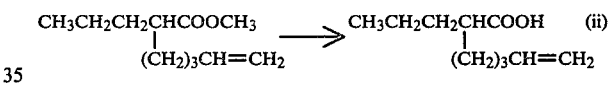

A mixture of methyl 2-propyl-6-heptenoate (1.8 g), sodium hydroxide (0.65 g), water (2 ml) and ethanol (100 ml) was heated under reflux for 2 hours. The solvent was removed under reduced pressure and the resulting residue was shaken with water and hexane. The aqueous layer was acidified with concentrated hydrochloric acid and extracted with ethyl acetate. The organic layer was dried and concentrated to give oil of 2-propyl-6-heptenoic acid (1.25 g).

IR spectrum: 1700, 1640 cm$^{-1}$ (neat)

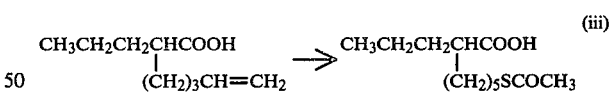

A mixture of 2-propyl-6-heptenoic acid (1 g) and thioacetic acid (450 mg) was heated for 4 hours at 60° C. and allowed to stand overnight at ambient temperature in an air-tight container. Excess thioacetic acid was evaporated under reduced pressure to give oil of 7-acetylthio-2-propylheptanoic acid (0.9 g).

PMR(CDCl$_3$,δ): 0.85(CH$_3$CH$_2$CH$_2$—), 2.20(—SCOCH$_3$, 11.2(—COOH)ppm.

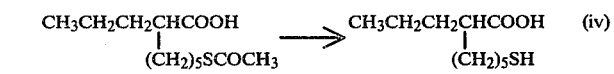

A solution of 7-acetylthio-2-propylheptanoic acid (0.8 g) in 5 N methanolic ammonia (50 ml) was stirred for 2 hours at ambient temperature in an argon atmosphere and concentrated to dryness under reduced pressure. The residue was dissolved in a small amount of a mixture of water and methanol and passed through a column of ion-exchange resin (Dowex 50W, H+ type). The eluate with a mixture of water and methanol was concentrated to dryness under reduced pressure to give semisolid of 7-mercapto-2-propylheptanoic acid (0.4 g).

IR spectrum: 1715 cm$^{-1}$ (neat).

Anal. calcd. for $C_{10}H_{20}O_2S \cdot \frac{1}{2}H_2O$: C,56.30;H,9.92;S,15,03%. Found: C,55.92;H,10.22;S,14.88%.

EXAMPLE 3

Preparation of 5-formyl-2-propylpentanoic acid

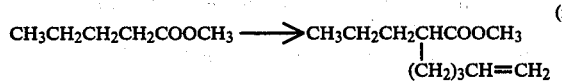

The procedure described in Example 2 (i) was repeated to yield methyl 2-propyl-6-heptenoate.

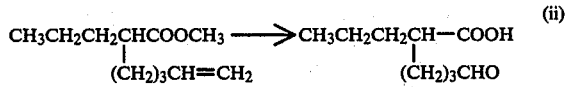

Ozone stream was bubled into a solution of methyl 2-propyl-6-heptenoate (2 g) in glacial acetic acid (80 ml) for 55 minutes at room temperature. Ether (100 ml) was added to the resulting mixture, followed by the portionwise addition of zinc powder (10 g) and water (1.1 ml) under cooling. The mixture was heated under reflux until KI-starch test became negative. After cooling, ether (100 ml) was added to the mixture, which was then filtered. The organic layer was separated, washed with water, dried and concentrated. The resulting residue was purified by silica gel column chromatography to give oil of methyl 5-formyl-2-propylpentanoate (1.1 g).

Rf value (TLC on silica, 0.2% methanol-chloroform) 0.5.

This compound was hydrolyzed in a manner similar to that in EXAMPLE 2(ii) to give oil of 5-formyl-2-propylpentanoic acid (0.85 g)

IR spectrum: 1700–1720 cm$^{-1}$ (neat).

PMR (CDCl$_3$,δ): 0.85($\underline{CH_3}CH_2CH_2$—), 9.70(—C$\underline{H}$O), 11.3(—COO$\underline{H}$).

EXAMPLE 4

Preparation of conjugate of 7-amino-2-propylheptanoic acid with Bovine Serum Albumin (BSA)

BSA(Bovine Serum Albumin fraction V, Armour Pharm.Co.,600 mg) was dissolved in 0.2 M phosphate buffer (pH 7.0,30 ml). To the solution was added an aqueous solution (adjusted to pH 7.0 with NaHCO$_3$, 30 ml) of 7-amino-2-propylheptanoic acid hydrochloride (prepared in Example 1, 180 mg), followed by the dropwise addition of 0.02 M aqueous glutaraldehyde solution (30 ml). The mixture was stirred for 2 hours at ambient temperature. After adding 1 M lysine solution (pH 7.5,3.0 ml), the mixture was further stirred for an hour and dialyzed for 48 hours against 0.15 M sodium chloride solution (2 liters) at 4° C., while the outer solution was renewed four times, then dialyzed against deionized water (2 liters) for 24 hours. The dialyzed solution was lyophilized to give the conjugate (550 mg).

EXAMPLE 5

Preparation of conjugate of 7-mercapto-2-propylheptanoic acid with BSA

A solution of 7-mercapto-2-propylheptanoic acid(prepared in Example 2, 150 mg) in 0.1 M phosphate buffer (pH 7.0,10 ml) was added to a solution of BSA(350 mg) in 0.1 M phosphate buffer (pH 7.0,30 ml) in an argon atmosphere. To the solution was added slowly a solution of N-(m-maleimidobenzoyloxy)succinimide (hereinafter referred to as m-MBS, 150 mg) in dioxane (10 ml). The mixture was stirred for 3 hours at ambient temperature, and dialyzed overnight against running water. The dialized solution was adjusted to pH 8.5 with 1 N sodium hydroxide solution and concentrated to about 10 ml by ultrafiltration using PM30 membrane (Amicon Corp.). The concentrate was adjusted to pH 4.5 with diluted hydrochloric acid and left in a cold place for 20 hours. The resulting precipitates were collected by centrifuge (10000 r.p.m., 15 minutes), suspended in a small amount of water, dissolved by adjusting to pH 8.5 with diluted alkali solution and dialyzed for 48 hours against 0.9% sodium chloride solution (2 liters), while the outer solution was renewed four times. The dialyzed solution was lyophilized to give the conjugate (330 mg).

EXAMPLE 6

Preparation of conjugate of 5-formyl-2-propylpentanoic acid with Bovine Serum Globulin(BSG)

A solution of 5-formyl-2-propylpentanoic acid (prepared in EXAMPLE 3, 172 mg) in methanol (5 ml) was added to a solution of BSG (600 mg) in phosphate buffer (pH 7.0, 40 ml) and allowed to react for an hour. To the mixture was added sodium cyanoborohydride (68 mg). The reaction mixture was stirred for 24 hours at 4° C. and dialyzed for 48 hours against 0.02 M phosphate buffer saline (5 liters) at 4° C., while the outer solution was renewed thrice. The dialyzed solution was lyophilized to give the conjugate (550 mg).

EXAMPLE 7

Preparation of conjugate of 7-amino-2-propylheptanoic acid with β-galactosidase

A solution of 7-amino-2-propylheptanoic acid hydrochloride (prepared in EXAMPLE 1, 11.2 mg) in water (0.5 ml) was neutralized with sodium hydrogen carbonate. To the solution was added a solution of m-MBS(15.5 mg) in dioxane (0.5 ml) and allowed to react for 30 minutes at ambient temperature. Then the solution (0.4 ml) was added to a mixture of β-galactosidase (Boeringer Mannheim G.m.b.H., 5 mg/ml suspension in ammonium sulfate solution, 100 μl) in 0.1 M phosphate buffer (pH 7.0, 2 ml) and allowed to react for an hour at ambient temperature. The reaction mixture was applied on a BioGel P-4 (BioRad Corp.) type I column (2.5×25 cm) equilibrated with 0.9% sodium chloride-0.02 M phosphate buffer, and eluted with the same buffer to obtain 5 ml fractions. The β-galactosidase activity of each fractions were measured. Fractions (Nos. 6–8) with high enzyme activity were combined and stored in a 0.1% sodium azide (preservative) and 0.1% BSA (stabilizer) solution.

EXAMPLE 8

Preparation of conjugate of 7-mercapto-2-propylheptanoic acid with β-galactosidase A solution of β-galactosidase from *Escherichia coli* (Boeringer Mannheim G.m.b.H., 5 mg) in 0.02 M phosphate buffer saline (pH 7.0, 3 ml) was dialyzed for 24 hours against the same buffer (1 liter) at 4° C., while the outer solution was once renewed. The dialyzed β-galactosidase solution was brought up to 5 ml with the addition of the same buffer. The solution (0.2 ml) was added to 0.2 M phosphate buffer (pH 7.0, 2 ml). To the mixture was added a solution (50 mg/ml, 0.05 ml) of 7-mercapto-2-propylheptanoic acid (prepared in EXAMPLE 2) in an argon atmosphere, and then a solution (8 mg/ml, 50 μl) of m-MBS in dimethylformamide. The mixture was stirred for 1.5 hours at ambient temperature and dialyzed overnight against 0.02 M phosphate buffer saline (pH 7.0, 2 liters) at 4° C. The dialyzed solution was applied on a Sephadex G25 column (2×25 cm) equilibrated with 0.02 M phosphate buffer saline, and eluted to obtain 5 ml fractions. Fractions (Nos. 6 and 7) with high β-galactosidase activity were combined and stored as a 0.1% sodium azide (preservative) and 0.1% BSA (stabilizer) solution for a stock enzyme-labelled antigen solution for enzymoimmunoassay of valproic acid.

EXAMPLE 9

Preparation of conjugate of 5-formyl-2-propylpentanoic acid with β-galactosidase A solution (500 μl) of β-galactosidase (500 μg) from *Escherichia coli* dialyzed against 0.02 M phosphate buffer saline was added to 0.2 M phosphate buffer (4 ml). To the mixture was added a solution (0.2 ml) of 5-formyl-2-propylpentanoic acid (2 mg) in methanol and the mixture was stirred for an hour at ambient temperature. Then sodium cyanoborohydride (2 mg) was added to the mixture and the mixture was further stirred for an four. The reaction mixture was dialyzed for 24 hours against 0.02 M phosphate buffer saline (pH 7.0, 2 liters). The dialized solution was applied on Sephadex G25 column (2×25 cm) equilibrated with 0.02 M phosphate buffer saline (pH 7), eluted with the same buffer to obtain 5 ml fractions. Fractions (Nos. 6 and 7) with high β-galactosidase activity were combined and stored at 4° C. after adding sodium azide (10 mg) and BSA(10 mg).

EXAMPLE 10

Preparation of antiserum

The conjugate of valproic acid derivative with BSA or BSG prepared in EXAMPLES 4, 5 or 6 was dissolved in 0.9% aqueous sodium chloride solution to make a 1% solution. An equal volume of complete Freund's adjuvant was added to the solution and mixed to form a w/o type emulsion. The emulsion (1.0 ml) was injected into the pads (0.1 ml×2 places) and the dorsal skin (0.1 ml×8 places) of rabbits. After two weeks, the emulsion (0.5 ml) was injected again into the dorsal skin (0.1 ml×5 places) of the same rabbits. The injection was repeated six times at two week intervals. Ten days after the final injections the rabbits were bled in order to prepare anti-valproic acid antiserum.

EXAMPLE 11

Preparation of insoluble antibody

To the antiserum (5 ml) prepared in EXAMPLE 10 was added 0.1 M phosphate buffer (pH 7.0, 5 ml) and saturated ammonium sulfate solution (10 ml) under ice-cooling. The mixture was stirred for 20 minutes and centrifuged at 12000×g for 10 minutes to collect precipitates. The precipitates were dissolved in 0.1 M phosphate buffer (pH 7.0, 5 ml), reprecipitated with addition of equal amount of saturated ammonium sulfate solution and centrifuged at 12000×g for 10 minutes. The process was repeated twice and the obtained precipitates were dissolved in 0.1 M phosphate buffer (pH 7.0, 5 ml). The solution was dialyzed for 24 hours against 0.9% sodium chloride-0.02 M phosphate buffer (pH 7.0, 2 liters) at 4° C. to obtain IgG-fraction (7 ml) of anti-valproic acid antiserum.

To a mixture of IgG-fraction (7 ml), cell walls of Lactobacillus plantarum (100 mg), water (11.6 ml) and 1 M acetate buffer (pH 4.9, 1 ml) was added 25% aqueous glutaraldehyde solution (0.4 ml) with stirring. The mixture was stirred for 2 hours at ambient temperature and centrifuged at 12000×g for 10 minutes to collect precipitates. The precipitates were washed three times with 0.1% BSA-0.9% sodium chloride-0.1% sodium azide-0.04 M phosphate buffer (50 ml) using a centrifuge and suspended in the same buffer (25 ml).

EXAMPLE 12

Preparation of a kit for immunoassay of valproic acid in blood (a kit for 50 assays)

(1) Standard solution "200"

Sodium valproate (2.0 mg) was dissolved in water (100 ml). The solution (10 ml) was placed in a 100 ml volumetric flask, mixed with normal human serum (10 ml) and sodium azide (100 mg), and diluted to make a final volume of 100 ml.

(2) Standard solution "100"

The standard solution "200" was diluted twofold with 0.1% sodium azide-10% normal human serum to prepare the standard solution "100".

(3) Standard solution "50"

The standard solution "100" was diluted twofold with 0.1% sodium azide-10% normal human serum as described in (2) to prepare the standard solution "50".

(4) Standard solution "25"

The standard solution "50" was diluted twofold with 0.1% sodium azide-10% normal human serum as described in (2) and (3) to prepare the standard solution "25".

(5) Standard solution "10"

The standard solution "100" was diluted tenfold with 0.1% sodium azide-10% normal human serum to prepare the standard solution "10".

(6) Standard solution "0"

This was 0.1% sodium azide-10% normal human serum.

Each solution (1 ml) described in (1)-(6) was placed in a 3 ml brown colored bottle.

(7) Enzyme-labelled antigen

The solution of conjugate of 7-amino-2-propylheptanoic acid with β-galactosidase (110 μl) prepared in EXAMPLE 7 was diluted with 0.1% BSA-0.1% sodium azide-0.9% sodium chloride-0.04 M phosphate buffer (27.39 ml), and placed in a 30 ml brown colored bottle.

(8) Antibody

The suspension of insoluble antibody (1250 μl) prepared in EXAMPLE 11 was mixed with 0.25% cell wall-0.1% BSA-0.1% sodium azide-0.04 M phosphate buffer (10.75 ml), and placed in a 20 ml brown colored bottle.

(9) Substrate

Powdery 2-nitrophenyl-β-galactopyranoside (44 mg) was placed in a 10 ml brown colored bottle.

(10) Substrate diluent

40% (w/v) Ethylene glycol-1 mM magnesium chloride-0.1%-sodium azide (5.5 ml) was placed in a 10 ml brown colored bottle.

(11) Reaction stopping agent

1 M Dipotassium phosphate-sodium hydroxide buffer (pH 11, 20 ml) was placed in a 20 ml plastic bottle.

EXAMPLE 13

Method for determination of valproic acid in blood

Valproic acid in human blood was determined with the kit described in EXAMPLE 12 according to the following procedure.

Preparation of test sample—Human serum was diluted tenfold with purified water (diluted test sample).

Preparation of substrate solution—The substrate diluent substrate was poured into the bottle containing the substrate to make into a homogeneous solution.

Dilution of reaction stopping agent—The reaction stopping agent was diluted tenfold with purified water.

[Assay procedure]

The diluted test sample (100 μl) and the standard solutions (each 100 μl) were pipetted into each test tubes. The labelled antigen (each 500 μl) and the suspension of antibody (each 200 microliters) were pipetted into each test tube. Immediately, the test tubes were stirred and incubated for 60 minutes at 37° C. (During the incubation, the test tubes were stoppered with rubber caps). After incubation, the test tubes were stirred again and the mixtures therein were centrifuged (1000×g, 10 minutes) placing the test tubes upside down in order to stick the antibody to the inside wall of the caps. After centrifugation, the test tubes were placed in a normal position in order to return supernatants to the bottom of the test tubes, and the rubber caps with the antibody were removed.

The test tubes were placed in an incubator at 37° C. The substrate solution (each 100 liters) was added to each of the supernatants and the mixtures were incubated for 30 minutes. Then the diluted reaction stopping reagent (each 2.5 ml) was added to each of the mixtures to stop the enzyme reaction. Absorbance of the mixtures at 410 nm was measured against purified water and the concentrations of valproic acid in the samples were read from the standard calibration curve (FIG. 1).

EXAMPLE 14

Correlation with GLC

Blood levels of valproic acid in patient were measured according to the method described in EXAMPLE 13 using the kit described in EXAMPLE 12, and the measured values (Y) were compared with values (X) obtained by gas-liquid chromatography method (GLC method).

number of samples: n=62
correlation coeficient: r=0.985
regression equation: Y=0.95 X+0.554
mean value: $\overline{Y}$=52.3 (γ/ml)

mean value: $\overline{X}$=54.5 (γ/ml)

Figure 2:
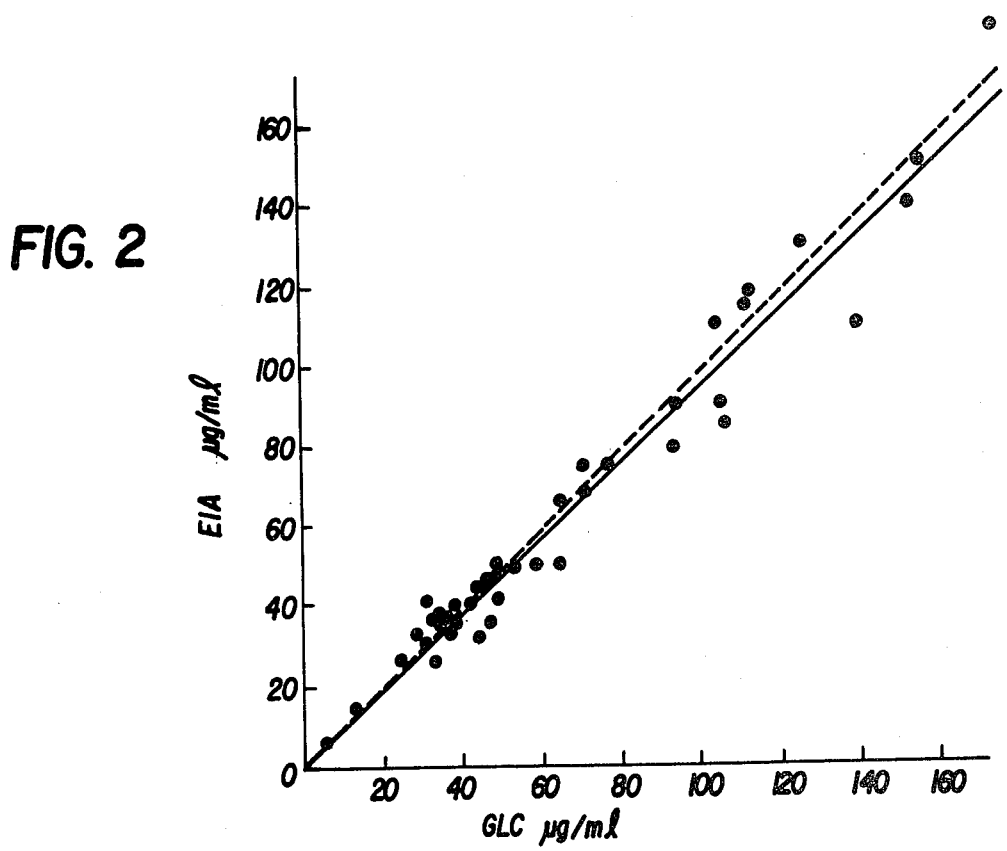

The both of the values were well correlated and it was confirmed that the blood level of valproic acid could be measured acculately using the EIA (enzymoimmunoassay) kit according to the invention (FIG. 2).

EXAMPLE 15

Cross reactivity with metabolites of Valproic acid

Cross reactivity of the antibody of the invention with metabolites of valproic acid known in human (R. Gugler and G. E. Unruch; Clinical Phamacokinetics, 5, 67–83 [1980]) was investigated (Table 3).

Although high cross reactivity was observed in 5-hydroxyvalproic acid (55%), 4-hydroxyvalproic acid (11%) and 2-propyl-3-pentenoic acid (13%), it is found that these compounds do not disturb the determination according to the invention, because blood levels of these compounds are extremely low (Table 3).

TABLE 3

Effect of metabolite of valproic acid on the antibody according to the invention

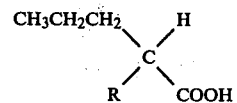

| R | Cross reactivity (%) | blood level (μg/ml) |
|---|---|---|
| CH₃CH₂CH₂— (valproic acid) | 100 | 200 |
| HOOCCH₂CH₂— | 3.8 | —* |
| HOCH₂CH₂CH₂— | 55 | trace |
| CH₃CH(OH)CH₂— | 11 | 0.3–2 |
| CH₃CH₂CH(OH)— | 5 | 5–10 |
| CH₃CH₂CO— | 0.7 | trace |
| CH₃CH=CH₂— | 13 | —* |
| CH₃CH₂CH= | 4 | 23 |
| HOCH₂CH₂CH₂— (δ-lactone) | 0.8 | trace |
| CH₃CH(OH)CH₂— (γ-lactone) | 0.15 | 1 |

*exsists only in urine

What is claimed is:

1. Compound of the formula:

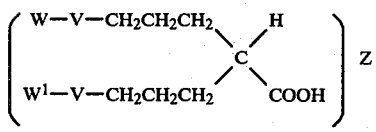

wherein
V is a bond or lower alkylene,
W is a bond to Z, or a group of the formula:

—CO—((U)$_p$(U$^1$)$_q$(U$^2$)$_r$),

—NH—((U)$_p$(U$^1$)$_q$(U$^2$)$_r$),

—S—((U)$_p$(U$^1$)$_q$(U$^2$)$_r$),

=CH—((U)$_p$(U$^1$)$_q$),

=C$_f$=N—((U)$_p$(U$^1$)$_q$(U$^2$)$_r$) or

—N=N— wherein
U is —NH—, —N=N—, —N=CH— or

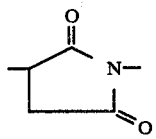

$U^1$ is lower alkylene, —O— lower alkylene— or lower arylene, $U^2$ is —O—, —CO—, —COO— or —O— lower arylene—, p,q and r are each 0, 1 or 2, and t is 0 or 1, $W^1$ is hydrogen atom, a bond to Z, or a group of the formula:

—CO—$((U)_p(U^1)_q(U^2)_r)$,

—NH—$((U)_p(U^1)_q(U^2)_r)$,

—S—$((U)_p(U^1)_q(U^2)_r)$,

=CH—$((U)_p(U^1)_q)$,

=C$_t$=N—$((U)_p(U^1)_q(U^2)_r)$ or

—N=N— wherein

U is —NH—, —N=N—, —N=CH— or

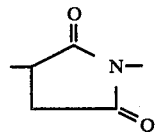

$U^1$ is lower alkylene, —O— lower alkylene or lower arylene, $U^2$ is —O—, —CO—, —COO— or —O— lower arylene, p, g and r are each 0, 1 or 2, t is 0 or 1, and Z is a protein, or salts thereof.

2. Compound according to claim 1, wherein $W^1$ is hydrogen atom and V is a bond.

3. Compound according to claim 1, wherein Z is albumin or globulin.

4. Compound according to claim 1, wherein Z is an enzyme.

5. A conjugate of a compound of the formula:

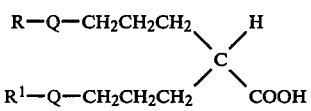

wherein

Q is a bond or lower alkylene,

R is —NH$_2$, —SH, —CHO, —COOH or —COCH$_2$—halogen, $R^1$ is hydrogen atom, —NH$_2$, —SH, —CHO, —COOH or —COCH$_2$—halogen, or salts thereof with an enzyme, wherein the enzyme is bonded to at least one of R and $R^1$ of the compound directly; or by one of the glutaraldehyde method, periodate method, dimaleimide method, N-(m-maleimidobenzoyloxy)succinimide method, mixed anhydride method, carbodiimide method, toluene diisocyanate method and diazo-method.

6. A conjugate according to claim 5 wherein $R^1$ is hydrogen atom and Q is a bond.

7. A conjugate according to claim 5 wherein said compound is selected from the group consisting of:

7-amino-2-propylheptanoic acid,
5-amino-2-propylpentanoic acid,
7-mercapto-2-propylheptanoic acid,
5-formyl-2-propylpentanoic acid, and
2-propylheptanedioic acid.

* * * * *